United States Patent
Keil et al.

(10) Patent No.: US 10,217,014 B2
(45) Date of Patent: Feb. 26, 2019

(54) METHOD AND DEVICE FOR PLANNING A RECORDING IN MEDICAL IMAGING

(71) Applicant: Siemens Healthcare GmbH, Erlangen (DE)

(72) Inventors: Miriam Keil, Erlangen-Dechsendorf (DE); Peter Schmitt, Weisendorf (DE)

(73) Assignee: Siemens Healthcare GmbH, Erlangen (DE)

( * ) Notice: Subject to any disclaimer, the term of this patent is extended or adjusted under 35 U.S.C. 154(b) by 139 days.

(21) Appl. No.: 15/360,354

(22) Filed: Nov. 23, 2016

(65) Prior Publication Data
US 2017/0154231 A1 Jun. 1, 2017

(30) Foreign Application Priority Data
Nov. 26, 2015 (DE) .................. 10 2015 223 457

(51) Int. Cl.
| | | |
|---|---|---|
| *G06K 9/00* | (2006.01) | |
| *G06K 9/20* | (2006.01) | |
| *A61B 5/055* | (2006.01) | |
| *A61B 6/03* | (2006.01) | |
| *A61B 8/13* | (2006.01) | |
| *G06K 9/32* | (2006.01) | |
| *A61B 5/00* | (2006.01) | |

(52) U.S. Cl.
CPC .......... *G06K 9/2081* (2013.01); *A61B 5/0033* (2013.01); *A61B 5/055* (2013.01); *A61B 6/032* (2013.01); *A61B 8/13* (2013.01); *G06K 9/3233* (2013.01); *G06K 2209/05* (2013.01); *G06T 2207/20104* (2013.01)

(58) Field of Classification Search
CPC .............. G06K 9/2081; G06K 9/3233; G06K 2209/05; A61B 6/032; A61B 5/0033; A61B 5/055; A61B 8/13; G06T 2207/20104
See application file for complete search history.

(56) References Cited

U.S. PATENT DOCUMENTS

| | | | | |
|---|---|---|---|---|
| 5,689,577 | A * | 11/1997 | Arata ...................... | G06T 17/20 345/423 |
| 9,295,434 | B2 * | 3/2016 | Herold ................... | A61B 6/032 |
| 2005/0264286 | A1 | 12/2005 | Harder | |
| 2008/0205725 | A1 | 8/2008 | Schmitt et al. | |
| 2010/0054561 | A1 * | 3/2010 | Khare ................... | G06T 11/006 382/131 |
| 2012/0116219 | A1 * | 5/2012 | Miller .................. | A61B 8/4254 600/438 |
| 2015/0332477 | A1 * | 11/2015 | Aalto-Setala ......... | G06T 7/0016 382/133 |

* cited by examiner

*Primary Examiner* — Shefali D Goradia
(74) *Attorney, Agent, or Firm* — Schiff Hardin LLP (57) ABSTRACT

In a method and apparatus for planning a data acquisition of a region of interest of an object under examination in medical imaging, wherein the region of interest is larger than a region of sensitivity of the medical imaging apparatus, a level of detail corresponding to the user's requirements is enabled by the planning including the division of the region of interest into at least two sub-regions based on at least one predefined parameter, and raw medical data are recorded from each of the at least two sub-regions.

14 Claims, 1 Drawing Sheet

METHOD AND DEVICE FOR PLANNING A RECORDING IN MEDICAL IMAGING

BACKGROUND OF THE INVENTION

Field of the Invention

The present invention concerns a method for planning a region of interest of an object under examination in medical imaging, wherein the region of interest is larger than a region of sensitivity of a medical imaging apparatus. The present invention also relates to a medical imaging apparatus, a computer program product and a computer-readable data storage medium designed to implement such a method.

Description of the Prior Art

Medical imaging apparatuses are able to generate image data from patients or other objects under examination. To this end, the region of interest of the patient has to be positioned in the region of sensitivity (field of view) of the medical imaging scanner so that the medical imaging scanner can acquire raw data from the region of interest, process the raw data if necessary, and display it as image data. For example, with whole-body examinations, it can be the case that the region of interest is larger than the region of sensitivity of the medical imaging scanner. For complete the acquisition of the region of interest, this region of interest is typically divided into sub-regions that are acquired on an individual basis.

In the final images used by a doctor for diagnosis or for planning an examination, the spatial connection of two contiguous sub-regions should preferably be fluid. Nevertheless, for segments of the region of interest, it may be desirable to have a more detailed depiction or to adapt the cross-section of the region of interest to the object under examination. This can enable the exclusion of regions that are not relevant for a diagnosis and/or the duration of the examination can be reduced.

Overall, a division of the region of interest into sub-regions enables a user to make significantly more changes and adaptations specific to the patient than is the case with a data acquisition of a region of interest that does not require division into sub-regions. Moreover, the visualization of the planning of sub-regions and their composition is complex. Well-trained users can use the visualized material made available to make individual adaptations that are tailor-made for a patient, to generate higher quality image data and/or to reduce the data acquisition time. Less well-trained users or users who have been instructed to make a data acquisition, in which the individual sub-regions differ only in the region to be depicted, can be distracted by the number of adaptation possibilities available, and the different visualization options. This can delay the planning.

SUMMARY OF THE INVENTION

An object of the invention to provide a method for planning a section-by-section data acquisition of a region of interest in medical imaging that enables a level of detail corresponding to the user's requirements. It is also an object of the invention to provide an imaging apparatus and a non-transitory, computer-readable data storage medium designed to implement such a method.

The method according to the invention for planning a data acquisition of a region of interest of an object under examination in medical imaging wherein the region of interest is larger than a region of sensitivity of a medical imaging apparatus includes a planning phase with the following method steps. The region of interest is specified by a user as an input into a computer. The computer is also provided with at least one predefined parameter. The computer automatically plans the data acquisition, including an automatic division of the region of interest into at least two sub-regions based on the at least one predefined parameter.

During medical imaging, image data are compiled that depict the anatomy or internal structure of an object under examination in the form of sectional views or projections. An object under examination can be a patient, a training volunteer or a phantom. A medical imaging apparatus is a system designed to carry out such medical imaging. Examples of medical imaging apparatuses include X-ray and ultrasound devices and computed tomography apparatuses and magnetic resonance tomography apparatuses.

In medical imaging, it is possible to compile image data from either the entire object under examination or from a segment, i.e. a partial volume of the object under examination. The volume to be depicted or the region to be imaged of the object under examination is the region of interest. This is typically selected depending upon the medical issue in question and individually for an object under examination and accordingly can vary in size.

Every medical imaging apparatus has a specified region of sensitivity, i.e. a measurement volume, wherein image data can be acquired from the segment or part of the object under examination located in the measurement. The region of sensitivity typically has a fixed spatial relationship to the medical imaging, or the scanning thereof. Therefore, during an examination of an object under examination, it is necessary for the region of interest to be incorporated in the region of sensitivity of the medical imaging apparatus so that the medical imaging apparatus is able to generate image data from said region.

If the size, i.e. the spatial expansion of the region of interest is greater than the size of the region of sensitivity, the complete acquisition of the region of interest can require a change to the position of the region of interest relative to the medical imaging apparatus. This can be performed stepwise or also continuously and the execution is dependent upon the imaging modality. For example, with ultrasound examinations, the spatial relationship between the region of interest and the region of sensitivity can be changed by moving the ultrasound probe, but in the case of tomography apparatuses with which the patient is placed on a bed or a table in a scanner, it may be necessary for a bed movement or table movement to be coordinated with the imaging, possibly stepwise.

If the region of interest that is larger the region of sensitivity of the medical imaging apparatus is acquired stepwise, segments of the region of interest are introduced into the region of sensitivity of the medical imaging apparatus in temporal succession. For complete imaging of the region of interest, it is necessary to divide the region of interest into several sections or sub-regions. The final image, which, for example, can be displayed to a doctor on a monitor ideally displays the entire region of interest in one image, even if the region of interest is larger than the region of sensitivity. Consequently, the region of interest should have uniform contrast and it should not be possible to identify the edge or border of a region of sensitivity.

The method according to the invention concerns the planning phase in which the division of the region of interest that is larger than the region of sensitivity of the medical imaging apparatus takes place. Initially, a region of interest is specified by a user. A user is typically a person using or operating the medical imaging apparatus. For the specification of the region of interest, the user preferably selects the region of the object under examination to be depicted, wherein the user can select the region of interest without knowing the size of the region of sensitivity. The selection can be made via a graphics interface of a computer, but in any event is eventually entered into the computer as an electronic input.

Moreover, at least one predefined parameter is provided to the computer. The planning is performed by a planning processor of the computer. A predefined parameter can be a numeric or a non-numeric value that can influence the division of the region of interest into sub-regions. One example of a numeric value of a predefined parameter is a maximum duration for the data acquisition of the region of interest. Non-numeric values can be relative descriptions of a required image quality at transitions between two sub-regions. The at least one predefined parameter can exist before the start of the method according to the invention or be specified by the user. Multiple predefined parameters are typically stored in a memory accessible by the planning processor and the selected or designated predefined parameter is retrieved from the memory.

The at least one predefined parameter provided is used as the basis of the planning, including the automatic division of the region of interest into at least two sub-regions. This planning can be performed without the interaction of a user of the medical imaging apparatus, i.e. without requiring any action on the part of a person operating the medical imaging apparatus during the examination of the object under examination. The region of interest is thereby divided into at least two sub-regions, wherein the predefined parameter provided or at least one of the predefined parameters provided, is taken into account. The method according to the invention can also take account of all the predefined parameters provided.

The at least one predefined parameter can be used as the basis for determining or deriving at least one further parameter required for the automatic division of the region of interest into sub-regions. If, for example, the size of the region of interest and the minimum overlap area are specified as predefined parameters, it is possible to determine the size of the sub-regions therefrom. The size of the sub-regions can be used as the basis for the automatic division of the region of interest into sub-regions.

The combined size of the sub-regions includes the region of interest, wherein the at least two sub-regions can be disjoint or can overlap. Typically, the boundaries of the sub-regions are selected such that adjacent sub-regions overlap so that the transition between the adjacent sub-regions in the combined image is as fluid as possible. To this end, it is also possible for interpolation or elastic registration to be used in the overlap area.

Following the end of the planning of the automatic division of the region of interest, raw medical data can be acquired from each of the at least two sub-regions. Medical raw data contains all the information of the sub-region or region of interest to be depicted that is required by the medical imaging apparatus to generate the image data of the sub-region or of the region of interest. The raw medical data are acquired for each sub-region. This typically means that, initially, a first sub-region is positioned such that it is completely included in or covered by the region of sensitivity of the medical imaging scanner and then the raw medical data of the first sub-region is acquired. After this, a second sub-region of the region of interest in brought into the region of sensitivity of the medical imaging scanner usually by repositioning either the object under examination or a component of the medical imaging scanner. As a result, it is now possible to acquire the raw medical data of the second sub-region. A similar procedure is used if further sub-regions are present. Unlike the stepwise acquisition explained, the raw medical data of the individual sub-regions can also be acquired continuously for the individual sub-regions. In this case, the individual sub-regions are not positioned consecutively in the region of sensitivity, but the entire region of interest is preferably moved relative to the region of sensitivity so that, during the movement of the region of interest, each sub-region is entirely included in the region of sensitivity at at least one time.

It is possible, such as after any processing required, to generate image data depicting the sub-regions individually from the acquired raw medical data of the individual sub-regions. Preferably, following the conclusion of the acquisition of the raw medical data of sub-regions, image data are generated depicting the entire region of interest. This image data, which be two-dimensional or three-dimensional, can be displayed to a user on a display unit, for example on a monitor.

An advantage of the method according to the invention is that the planning of the division of a large region of interest into sub-regions is performed while observing at least one predefined parameter such that it is possible to record corresponding raw medical data. In this case, the user does not have to make any changes or adaptations since the sub-regions are planned automatically by the planning processor in dependence upon the at least one parameter. Consequently, the at least one predefined parameter is decisive for the accuracy or the details of the adaptation of the sub-regions to the region of interest and to the medical issue in question. The larger the number of predefined parameters, the more accurately it is possible to adapt the at least two sub-regions to the individual region of interest and to any possible additional requirements. Consequently, no special prior knowledge on the part of the user with respect to planning for large regions of interest is required and it is possible to ensure user-independent, standardized quality of the image data.

In an embodiment of the method according to the invention, the at least one predefined parameter describes a relationship between the region of interest and the at least two sub-regions.

Consequently, a predefined parameter can, for example, specify the number of sub-regions into which the region of interest is to be divided or a size of the individual sub-regions to be achieved on the automatic division of the region of interest. Alternatively, the predefined parameter can also specify an overlap area between two sub-regions, i.e. a measure of the degree to which spatially adjacent sub-regions overlap or the width of the boundary area recorded by the two sub-regions. It is generally also possible for the predefined parameter to specify limit values, i.e. minima or maxima, for the examples given.

For example, it is particularly advantageous for a predefined parameter to specify the spatial size of the region of sensitivity as the maximum size of a sub-region. This makes it possible to ensure during the determination of sub-regions of the region of interest that the raw medical data of the sub-regions can be recorded in one step. In this case, the spatial size can be defined as a three-dimensional volume; maximum spatial expansion along a spatial direction is also conceivable.

If a predefined parameter specifies the minimum overlap area of adjacent sub-regions, it is possible to ensure that no sharp edge is visible between sub-regions in the final combined image. On the other hand, when a fixed or maximum overlap area between sub-regions is specified as a parameter, it is possible to ensure that only a limited part of the raw medical data is recorded twice during in images of two adjacent sub-regions. It is frequently advantageous for the acquisition of raw medical data to be kept as low as possible since the amount of raw medical data to be recorded can, for example, correlate with the energy dose applied in computed tomography and with the acquisition time in magnetic resonance tomography.

In another embodiment of the method, the at least one predefined parameter is defined before the provision of the at least one predefined parameter by a user in accordance with the object under examination.

Consequently, in this variant of the method, a user of the medical imaging apparatus, i.e. the person operating or using the system, who uses or controls the system during the examination of the object under examination, specifies a first parameter before this first parameter is provided and used for planning the data acquisition of the object under examination. For example, during a whole-body examination of a patient, the user can specify the maximum two-dimensional axial spatial expansion of the patient as a first parameter. The user can specify this information via an input unit of the medical imaging apparatus of the planning processor, for example.

An advantage of this embodiment according to the invention is that the user can specify at least one parameter that is taken into account during the planning of the data acquisition. This enables properties of the sub-regions to be adapted to an object under examination. Nevertheless, users do not have to perform the planning themselves or intervene in the planning. Consequently, no special prior knowledge on the part of the user with respect to the planning of large regions of interest is required.

In a further embodiment of invention, the region of interest is displayed to the user in the planning phase similarly to a normal region of interest which is smaller than the region of sensitivity of the medical imaging apparatus and the user has the option of adapting the region of interest displayed.

A normal region of interest is a segment of the object under examination to be depicted, which can be typically depicted by means of the medical imaging apparatus used, wherein no change to the position of the object under examination and/or the region of sensitivity of the medical imaging apparatus is necessary. Consequently, the spatial expansion of a normal region of interest in all spatial directions is smaller than the spatial expansion of the region of sensitivity of the medical imaging scanner in the spatial directions or is at most equally as large. The region of sensitivity thus can include a normal region of interest. Depending upon the type of medical imaging apparatus, the maximum absolute size of the normal region of interest can be determined from this relationship.

When specifying the region of interest, the user can proceed as if selecting a normal region of interest. In this case, the user is preferably not given any indication that the selected region of interest is larger than the region of sensitivity, at least in one direction. In this way, the region of interest can be displayed to the user as if no division into sub-regions were necessary.

Unlike the case when planning a normal region of interest, the specification of the region of interest can be subject to restrictions or boundary conditions that may possibly offer the user less freedom of choice than is the case with a normal region of interest. It is conceivable for the construction of a medical imaging apparatus to limit the spatial expansion of a region of interest in at least one direction, such as, for example, is the case with magnetic resonance apparatuses for directions perpendicular to the basic magnetic field.

It is also possible to dispense with the depiction of the information relating to the division of the region of interest into the sub-regions for a user following the automatic division of the region of interest into at least two sub-regions by the planning processor. Hence, the complexity of the multi-stage data acquisition of the region of interest due to the division into sub-regions can be hidden from the user.

A further embodiment of the invention provides that, in an additional planning phase, a user specifies a property of a sub-region before the data acquisition of raw medical data of the sub-region taking account of the property.

This additional planning phase according to the invention can take place following the planning of the data acquisition based on at least one predefined parameter. The additional planning phase is optional and can be actively initiated by the user. During the planning of the data acquisition, the region of interest is automatically divided into a plurality of sub-regions, wherein the specified parameters are taken into account. The predefined parameters typically influence the relationship between the entire region of interest and the sub-regions and are therefore also used for the division of the region of interest. Predefined parameters usually relate not to an individual sub-region, which means that they do not specify any information or properties for a special section of the region of interest, but advantageously define the composition or configuration of the sub-regions. The advantage of planning the data acquisition on the basis of the predefined parameter consists in the fact that the user does not have to make any adaptations, thus enabling errors to be avoided.

If it is necessary to perform a data acquisition that is particularly detailed or individually adapted to a patient or the reason for the examination, in addition to the described planning of the data acquisition, typically adaptations and/or changes to the sub-regions are required. This can be implemented or enabled in accordance with inventive variant of the method explained here.

Consequently, the user can specify a property for an individual sub-region, which is taken into account or observed during the data acquisition of the raw medical data of this sub-region. In this way, the user can influence the data acquisition of the sub-region by the specification of the property in the same way that the user can also influence the data acquisition of an entire region of interest, which, as a result of its size, does not have to be divided into sub-regions. Accordingly, the pre-specifiable properties are determined by the imaging modality and the medical imaging apparatus. Examples of properties that can be specified by the user include the resolution of the image data of a sub-region that the user is able to change, i.e. increase or reduce, or schemes for the acquisition of raw medical data and breathing commands. Similarly, the user can, for example, specify that a data acquisition of a sub-region is performed several times, possibly with different properties specified by the user for the sub-region.

The method according to the invention is not restricted to the specification of only one property of a sub-region by the user. Instead, the user can specify properties for two or more sub-regions of the region of interest which are observed during the data acquisition. The properties for different sub-regions can be the same or also different.

It is also possible for a further method step to be necessary in order to take account of the property specified by the user during the data acquisition of the raw medical data. The property is taken into account during the data acquisition of a sub-region in addition to the predefined parameters specifying the division into sub-regions. The specification of a property for a first sub-region may possibly also relate to further properties or parameters of the first sub-region or even other, for example adjacent, sub-regions. This relationship is advantageously checked before the commencement of the data acquisition of the first sub-region and matched to or consolidated with the properties of the other sub-regions.

Depending upon the property specified by the user, information on the object under examination and on the sub-regions defined by the planning can be necessary or helpful. This can be displayed to the user on a monitor. The specified property with respect to a sub-region and any further properties that may possibly result therefrom relating to the sub-region or further sub-regions can be visualized to the user, i.e. for example on the monitor. It is also conceivable for a property to be specified by visual control. For example, for a change to the size of a sub-region, it is not only possible to specify a numeric value, it is also possible for a boundary line to be shifted or moved by means of interaction on the monitor. In this way, the user can check the specified property and the influence thereof on further properties directly by visual means.

An advantage of the additional planning phase is that, before the data acquisition of large regions of interest, it is possible to perform a more detailed adaptation or planning which is tailor-made for the individual object under examination. Hence, the basic and feasible division of the region of interest into sections that takes place during the planning can be adapted by the user to the object under examination such that specifications such as imaging that is as detailed as possible or an examination time that is as short as possible are achieved. This is particularly recommended for a well-trained user who is able to cope with a number of properties and parameters and will not unintentionally change the results achieved in the planning of the data acquisition on the basis of the predefined parameters by the specification of properties. A less well trained user should not initiate the additional planning phase and correspondingly cannot undertake detailed planning and instead has to rely on a standardized quality of the image data.

In another embodiment of the method according to the invention, the specified property describes a spatial expansion of the sub-region.

Initially, the spatial expansion of all sub-regions is specified by the planning on the basis of the at least one predefined parameter. For example, in the case of a whole-body examination, a partial volume can cover the entire axial cross section of an object under examination and, in the longitudinal direction correspond to the maximum expansion of the region of sensitivity of the medical imaging apparatus in this direction. The method according to the invention enables the user to change the spatial expansion in at least one spatial direction, i.e. to change the size of the partial volume. Proceeding from the previous example, during a whole-body examination of the blood vessels located in the region of interest, i.e. in the entire body, it is possible for a partial volume to be reduced so that the partial volume is restricted to the region containing blood vessels. Thus, this enables severely bent vessels to be recorded with as little peripheral anatomy as possible. If the raw medical data of a smaller region is recorded, this can, on the one hand, be accompanied by a reduction in the amount of data or by an improvement in the image quality with the same amount of data. The advantages of a reduced amount of data apply, for example, to computed tomography devices or magnetic resonance tomography devices.

An advantage of this embodiment of the method is that the sub-regions can be individually adapted to the clinical issue in question, thus achieving improved image quality.

In another embodiment of the method, a first sub-region differs from an adjacent sub-region with respect to the property specified by the user for the first sub-region.

The user can specify a property for an individual sub-region, wherein that specification is not applicable for adjacent sub-regions. For example, different spatial expansions, i.e. variables, can be specified as properties for different sub-regions. This enables the user to make an individual adaptation of the sub-regions to the medical issue in question and to the object under examination.

In a further embodiment of the invention, a restriction is provided for the specification of a property of a sub-region.

The user can specify at least one property for a sub-region which is then taken into account or observed during the data acquisition of the sub-region. Users can typically specify such properties that they are able to specify or change in the case of the presence of regions of interest that do not require any division into sub-regions for the adaptation of the images to the object under examination and/or the medical issue in question. However, the scope of these properties can be restricted in that, for example, the value range of a numeric property is limited or one property cannot be specified for a sub-region. Alternatively, it is also possible for the properties to be assigned boundary conditions that have to be observed or applicable during the specification of the properties.

One example of a restriction in two-dimensional magnetic resonance tomography is the orientation of the slices of a sub-region to be depicted. If, for example, a whole-body coronal view is required for a patient, a division of the region of interest into sub-regions is typically required. In order to ensure continuity or uniformity of the coronal view in the entire region of interest, all the sub-regions should be recorded in the same orientation. It is only in this way that adjacent sub-regions can be aligned with respect to one another such that a medical diagnosis is meaningful. It is useful for boundary conditions for properties not to apply to all images equally, but to be dependent thereupon. For example, in angiography a spatially-continuous depiction of vessels over different sub-regions can require a variable sagittal orientation for different sub-regions.

Consequently, the advantage of restricting a property consists in the fact that the effect of the specification of a property for one sub-region on further sub-regions is taken into account and limited and hence a quality of medical image data that enables medical evaluation is ensured.

In another embodiment of the method according to the invention, information to be displayed spatially relating to the sub-regions is visualized to the user on a display unit of the medical imaging apparatus. For example, the boundaries of sub-regions resulting from the planning of the data acquisition represent information to be depicted spatially relating to the sub-regions. These boundaries can be displayed to a user on a monitor. Preferably, a depiction of the boundaries is stored with an image identifying the outline of the object under examination and possibly also reproduces the anatomy or the internal structure of the object under examination. The level of detail of the stored image is usually much lower than in the image data for which the data acquisition is planned using the stored image. The boundaries of the sub-regions can be depicted superimposed on the stored image.

The easiest-to-understand depiction of the information relating to the sub-regions to be depicted is the marking of the boundaries of the sub-regions, wherein adjacent sub-regions are only separated by a line. This enables the division of the entire region of interest into sub-regions to be displayed clearly to the user on the monitor.

The visualization explained is sufficient, but optional, when the additional planning phase in which the user can specify at least one further property is not carried out. The described depiction of the boundaries of the sub-regions is clear and does not require special training for the user. It is also possible to dispense with a depiction of the sub-regions for this user so that the user is not able or does not have to be aware of the automatic division into sub-regions.

It is also possible for more extensive information to be depicted spatially relating to the sub-regions to be depicted. This is in particular advisable during the performance of the additional planning phase in which the user specifies at least one further property, which is taken into account during the data acquisition of the raw medical data. In one simple embodiment, the overlap between two adjacent sub-regions be displayed and can be changed by the user in the additional planning phase. In the additional planning phase, the user is also able to specify navigators for individual spatial points in a sub-region or in a number of sub-regions or saturation regions within a sub-region or within a number of sub-regions. These individual spatial points or saturation regions can be displayed to the user. The information is preferably displayed with the stored image in the background. The boundaries of the sub-regions can also be visualized. It is also possible for adjacent sub-regions to be graphically linked so that the specification of a property can extend to a plurality of sub-regions and for not only one sub-region but all the graphically linked sub-regions to be recorded taking account of this property.

The visualization of such information is not bound to the additional planning phase but can also be displayed without the initiation of the additional planning phase by the user. However, this is subject to the condition that information that can be visualized is present. If no saturator or navigator is provided during the data acquisition, it is also not possible for this to be depicted. The amount and selection of the information to be visualized can preferably be configured in advance. During the configuration, preferably special attention is paid to a user's requirements and the information to be visualized is defined in dependence on the method step.

An advantage of this embodiment is that useful spatial information can be visualized for the user. In this case, the level of detail of the information can be matched to the user or is dependent on the properties specified in an additional planning phase. The method according to the invention enables application and user-specific visualization, thus enabling the avoidance of errors during the planning of a data acquisition.

In a further embodiment of the invention, the user specifies a first and a second property for at least one sub-region in the additional planning phase.

The user can use the divided sub-regions based on at least one predefined parameter as the basis for assigning a sub-region not only a first property but also a second property that has to be taken into account or observed during the data acquisition of the sub-region. In particular, before the data acquisition of all the sub-regions, the user can allocate to the sub-regions individually or to a number of sub-regions at once properties to be taken into account during the data acquisition of the respective sub-regions. Hence, the second property can relate to a different sub-region than the first property.

The advantage of this embodiment is that a user, in particular a trained user, can match numerous individual adaptations of the sub-regions and examination methods to the object under examination and to the individual medical issue in question.

In another embodiment of the method, premature termination of the additional planning phase is enabled. Accordingly, following the specification of at least one property of a sub-region, the user can prematurely terminate or abort the method according to the invention for planning a data acquisition of a large region of interest. This means that the data acquisition of the region of interest is not performed and all the specified properties for at least one sub-region are no longer available. Following the premature termination, the specified properties can no longer be visualized and no longer used for the data acquisition. Moreover, it is also possible for the planning with which the automatic division of the region of interest into sub-regions was performed to be undone. As a result, there are also no longer any sub-regions and the corresponding boundaries can no longer be depicted.

Accordingly, in advantage of this method is that, during complex or detailed planning of a data acquisition requiring the specification of a plurality of properties, the user can undo the specified properties or suspend the planning completely and start again from the beginning. This is in particular advantageous when properties are specified with boundary conditions or restrictions that were not taken into account for further properties and the desired properties can no longer be adapted for a data acquisition or can only be adapted with considerable effort. Hence, the user is able to undertake a new planning process, possibly on the basis of the existing sub-regions. This can have a time-saving effect with respect to the entire planning.

In a further embodiment of the invention, following the premature termination of the additional planning phase, the planning of an automatic division of the region of interest into at least two sub-regions takes place again based on the at least one predefined parameter.

According to this embodiment, on the premature termination, all the specified properties are reset or no longer visualized even when they relate to the division of the region of interest into sub-regions. The structuring into sub-regions is cancelled so that, following the premature termination of the additional planning phase, the region of interest is present and/or depicted as an entire unit. At least one predefined parameter is specified. In this case, the predefined parameter can correspond to the predefined parameter specified before the additional planning phase was carried out. Alternatively, it is also possible, possibly in addition to this predefined parameter, for a further predefined parameter to contain or reflect at least one property specified by the user in the prematurely terminated additional planning phase. For example, the at least one predefined parameter can be used to perform the planning, i.e. the automatic division of the region of interest into sub-regions, such that the subsequent data acquisition takes account of a property specified in the prematurely terminated additional planning phase without a new additional planning phase being required. The feasibility of this embodiment can depend upon the specified property and the boundary condition possibly associated therewith. For example, it is conceivable for the property describing a spatial expansion of the sub-region to be introduced into the planning as a predefined parameter, while a saturation range specified in the prematurely terminated additional planning phase is not used as a predefined parameter for the planning.

An advantage of this embodiment of the invention is that the planning of the automatic division of the region of interest is started anew following the premature termination of the additional planning phase and the user does not have to carry out any further planning steps. The resulting sub-regions are not yet influenced by the specification of properties and the user can optionally specify properties anew. This is in particular advantageous, if a user is overtaxed by the specification of complex properties. Moreover, the sub-regions displayed in the initial situation can reflect specified properties of the prematurely terminated additional planning phase.

The invention also encompasses a medical imaging apparatus having a computer with a planning processor, wherein the planning processor is designed (configured) to plan a data acquisition of a region of interest of an object under examination in accordance with the inventive method.

The invention enables the planning a data acquisition of a region of interest of an object under examination in medical imaging, wherein the region of interest is larger than a region of sensitivity of a scanner of the medical imaging apparatus. Subsequently thereto, it is possible to carry out the data acquisition of the raw medical data of the sub-regions. In this case, the user does not have to make any changes or adaptations since the sub-regions are planned by the planning processor in dependence on the at least one predefined parameter. If a predefined parameter specifies the minimum overlap area of adjacent sub-regions, it is possible to ensure that there are no sharp edges between sub-regions in the final assembled image. Consequently, no special prior knowledge on the part of the user with respect to the planning of large regions of interest is required. It is possible to carry out an additional planning phase so that, before the data acquisition of large regions of interest, it is possible to perform detailed adaptation or planning which is tailor-made for the individual object under examination.

The advantages of the medical imaging apparatus according to the invention substantially correspond to the advantages of the method according to the invention for planning a data acquisition of a region of interest of an object under examination as explained above in detail. The above-described features, advantages and alternative embodiments mentioned in this context are also applicable to the apparatus.

The invention also encompasses a non-transitory, computer-readable data storage medium encoded with programming instructions (program code) that, when the storage medium is loaded into a control computer system of a medical imaging apparatus, cause the control computer system to operate the medical imaging apparatus so as to execute the method according to the invention, and any or all embodiments thereof, as described above.

The program code can be software with a source code, which still has to be compiled and linked or only has to be interpreted, or an executable software code that only needs to be loaded into the computing unit or control device for execution.

DESCRIPTION OF THE PREFERRED EMBODIMENTS

Figure 1:
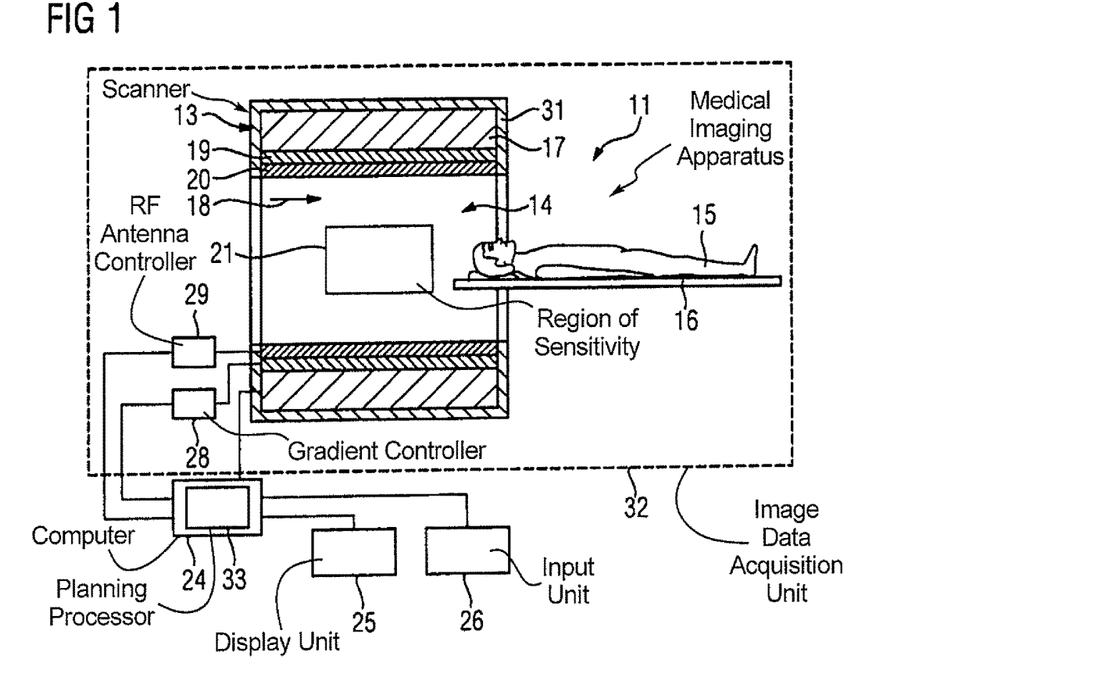
FIG. 1 a schematically illustrates a medical imaging apparatus according to the invention.

FIG. 1 schematically depicts a magnetic-resonance apparatus as an example of a medical imaging apparatus 11 according to the invention. The medical imaging apparatus 11 has a data acquisition scanner 13 with a basic field magnet 17 that generates a strong and constant basic magnetic field 18. The scanner 13 also has a cylindrical patient-receiving region 14 that receives an examination subject 15. The patient-receiving region 14 is cylindrically enclosed by the scanner 13 in a circumferential direction. The examination subject 15 can be moved into the patient-receiving region 14 by a patient-support 16 of the scanner 13. To this end, the patient-support 16 has an examination table that is movable within the scanner 13. The patient-receiving region 14 includes the region of sensitivity 21 of the scanner 13, which is thus also the region of sensitivity of the medical imaging apparatus 11. The segment or part of the examination subject 15 located in the region of sensitivity 21 is able to generate image data. In magnetic resonance tomography, the region of sensitivity is typically a cuboid or a cylinder lying parallel to the scanner 13. The center of the region of sensitivity 21 is typically in the isocenter of the scanner 13 and the spatial expansion of the region of sensitivity 21 parallel to the basic magnetic field 18 is usually approximately 40 cm. The scanner 13 is shielded from the outside by a housing shell 31.

The scanner 13 also has a gradient-coil arrangement 19 to generate magnetic-field gradients used for spatial encoding during imaging. The gradient-coil arrangement 19 is actuated by a gradient controller 28. The scanner 13 also has a radio-frequency antenna 20, which, in the case shown, is designed as a body coil permanently integrated in the scanner 13, and a radio-frequency antenna controller 29. The radio-frequency antenna 20 is actuated by the radio-frequency antenna controller 29 so as to emit radio-frequency pulse sequence into an examination volume substantially formed by the patient-receiving region 14. The emitted radio-frequency pulse sequence causes certain nuclear spins in the examination subject 15 to be deflected from the field lines of the basic magnetic field 18. As these excited nuclear spins relax, they emit radio-frequency magnetic resonance signals. The radio-frequency antenna 20 is further designed to receive the magnetic-resonance signals from the examination subject 15.

The medical imaging apparatus 11 has a computer 24 that controls the basic field magnet 17, the gradient controller 28 and the radio-frequency antenna controller 29. The computer 24 centrally controls the medical imaging apparatus 11, for the performance of a predetermined data acquisition sequence, such as a gradient-echo sequence. Control information, such as imaging parameters, and reconstructed magnetic-resonance image data, can be displayed to a user on a display unit 25, for example on at least one monitor, of the medical imaging apparatus 11. The medical imaging apparatus 11 also has an input unit 26 via which information and/or parameters can be entered by a user during a measurement process. The computer 24 can include the gradient controller 28 and/or the radio-frequency antenna controller 29 and/or the display unit 25 and/or the input unit 26.

The medical imaging apparatus 11 has an image-data-acquisition unit 32. The image-data-acquisition unit 32 is in the present case formed by the scanner 13 together with the radio-frequency antenna controller 29 and the gradient controller 28. The computer 24 further has a planning processor 33. Together with the input unit 26, the display unit 25, the computer 24 and the planning processor 33, the scanner 13 is designed to carry out the method according to the invention.

The medical imaging apparatus 11 depicted can obviously have other components that are conventionally present in magnetic resonance apparatuses. The general mode of operation of a magnetic resonance apparatus is known to those skilled in the art and so a more detailed description of the operation and the further components is not necessary herein.

Other types (modalities) of medical imaging apparatuses also enable the method according to the invention to be performed. Such further medical imaging apparatuses are known to those skilled in the art so that a more detailed description is not necessary herein.

Figure 2:
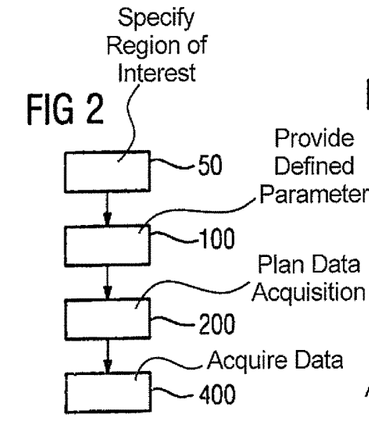
FIG. 2 is a flowchart of a first embodiment of the method according to the invention.

FIG. 2 is a flowchart of a first embodiment of the method according to the invention for planning a data acquisition of a region of interest of an object under examination 15 in medical imaging. The object of the method is to generate a data acquisition from an object under examination 15 located in the patient-receiving region 14 of a medical imaging apparatus 11. In this case, the specified region of interest is larger than the region of sensitivity 21 of the medical imaging apparatus 11. It is thus necessary for the spatial relationship between the object under examination 15 and the region of sensitivity 21, i.e. the medical imaging apparatus 11, to be changed. It is necessary to ensure that, with the image-data-acquisition unit 32, the medical imaging apparatus 11 acquires raw medical data from the entire region of interest so this region can be depicted in image data. In this case, it is possible to proceed in accordance with the method according to the invention.

In a first method step 50, the user specifies the region of interest. The specification of the region of interest can take place directly by inputting numeric values using the input unit 26 of the medical imaging apparatus 11 or by modifying boundary lines depicted on a display unit 25. Alternatively, the user can specify the region of interest indirectly, for example by stating that a head examination is to be performed on a patient. The computer 33 of the medical imaging apparatus 11 can process the information, determine a region of interest and specify said region.

In a second method step 100, at least one predefined parameter is provided. The at least one predefined parameter is typically stored in a memory of the programmable computer 24 and the planning processor 33 can preferably access said memory and provide the at least one predefined parameter. A predefined parameter can be stored by the manufacturer as a fixed value in a memory of the programmable computer 24. It is also conceivable for a predefined size to be defined before its provision by a user in accordance with the object under examination. Hence, if a predefined parameter is required during the further course of the method according to the invention, the planning processor 33 can make this predefined parameter available for the desired use.

A predefined parameter can influence the division of the region of interest in that, for example, it specifies limit values for the number of divisions or the size of the divided sections, the sub-regions, which can be positioned, for example, within the region of sensitivity 21 of the medical imaging apparatus 11. In the following method step 200, the planning of the data acquisition is performed in that the region of interest is divided into at least two sub-regions with reference to the at least one predefined parameter. This planning can be carried out by the planning processor 33. Information to be displayed spatially relating to the sub-regions can be visualized to the user on a display unit 25 of the medical imaging apparatus 11.

When the planning in the method step 200 is concluded and if the user of the medical imaging apparatus does not wish to or is unable to make any further adaptations, the raw medical data from each of the at least two sub-regions are recorded in method step 400. To this end, the planning processor 33 can transfer or make available the result of the planning of the computer 24 of the medical imaging apparatus 11. The computer 24 of the medical imaging apparatus 11 can use the results or information to start the acquisition of the raw medical data by the scanner 13 of the medical imaging apparatus 11. In method step 400, all the data required for the generation and acquisition of the raw medical data and for the generation of image data of the region of interest necessary is present.

Figure 3:
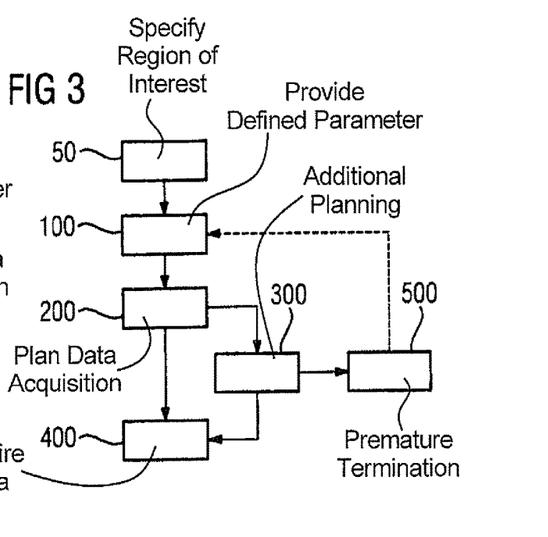
FIG. 3 is a flowchart of a second embodiment of the method according to the invention.

FIG. 3 is a flowchart of a second embodiment of the method according to the invention for planning a data acquisition of a region of interest. Unlike the first embodiment, this method enables the individual adaptation of the data acquisition to the clinical issue in question and to the object under examination by the user. In the first embodiment, the planning of the data acquisition does not require any interaction on the part of a user but is instead performed by the planning processor 33. In the second embodiment, a user or operator of the medical imaging apparatus 11 is able to make changes to the result specified or suggested by the planning processor 33 for the automatic division of the region of interest into sub-regions. The method in the second embodiment starts with the method steps 50, 100 and 200 described in detail in the first embodiment. It is also possible to link the data acquisition of raw medical data from each of the at least two sub-regions, i.e. method step 400, to the method step 200 so that the first method according to the invention is terminated at this point. In this case, the user does not adapt the sub-regions to the object under examination.

However, the user does have the option, following the conclusion of the planning of the automatic division of the region of interest into at least two sub-regions (method step 200) and before the commencement of the data acquisition of the raw medical data (method step 400), of specifying at least one property for at least one sub-region in an additional planning phase (method step 300). The method step 300 is optional. If a first property is specified for a first sub-region, the first property is also taken into account during the data acquisition of the raw medical data of the first sub-region. Following the specification of the first property, the user can also specify a second or more properties simultaneously or consecutively relating to the first sub-region or further sub-regions. The user can specify a property for a first sub-region, wherein the first sub-region differs from an adjacent sub-region with respect to the property specified by the user for the first sub-region.

A property can describe a spatial expansion of the sub-region for which the property was specified. For example, the user can influence the size or position of the sub-region by the specification of the property. It is also conceivable for restrictions to apply to the specification of a property. Therefore, for example, the user has less freedom in the specification of a property in comparison with the specification of properties for regions of interest that are not divided into sub-regions. These restrictions or boundary conditions can be defined by a desired uniformity of the entire region of interest.

The specification of the at least one property is performed by means of the input unit 26 of the medical imaging apparatus 11. The changes resulting from the specified properties can be visualized on the display unit 25, for example a monitor.

If the user has specified all the necessary or desired properties in method step 300 and/or the user agrees to with the visualized properties of the sub-regions, method step 400, i.e. also the data acquisition of the raw medical data from each of the at least two sub-regions, can be performed. If the user does not agree to the changes to the sub-regions effected by the user by the specified properties and if the user can no longer undo the changes as desired or specify further properties so that the sub-regions are recorded in the intended way, premature termination of the method according to the invention is provided in method step 500. Method step 500 does not provide for any data acquisition of the raw medical data (method step 400) of the sub-regions in the form as specified by method step 300. Instead, it is optionally possible, following the premature termination (method step 500), to start anew with the provision of a predefined parameter (method step 100) which is used as the basis for the division of the region of interest into at least two sub-regions (method step 200). In this case, the method can be continued in accordance with the description for method step 300 or method step 400.

In method step 400, the image-data-acquisition unit 32 can acquire the raw medical data of the individual sub-regions. To this end, in magnetic resonance tomography, a magnetic-resonance-actuation sequence has to be performed by the magnetic-resonance apparatus. The magnetic-resonance-actuation sequence is embodied such that the specifications for the sub-regions are retained during the generation of the image data. To this end, the computer 24 is configured to control the magnetic-resonance-actuation sequence with the specified properties and to actuate the gradient controller 28 and/or the radio-frequency-antenna controller 29 in accordance with the specifications of the magnetic-resonance-actuation sequence. During the performance of the magnetic-resonance-actuation sequence, the raw medical data are recorded by the scanner 13. This raw medical data can be recorded separately for each sub-region, or continuously for the entire region of interest while the region is moved relative to the region of sensitivity 21. The raw medical data can be processed separately for each sub-region; optionally, the image data of the sub-regions can be reconstructed and then combined to form one image depicting the entire region of interest. Alternatively, the raw medical data of the individual sub-regions can be processed as a common data set so that the image data of the entire region of interest can be reconstructed directly. The image data can be depicted to the user on the display unit 25.

The method steps of one embodiment of a method according to the invention depicted in FIGS. 2 and 3 are carried out by the computer 24 that includes the planning processor 33, together with the scanner 13. To this end, the planning processor 33 has the necessary software and/or computer programs, which are stored in a memory of the planning processor 33. The software and/or computer programs have program code that causes the method according to the invention to be implemented when the computer code is executed in the planning processor 33.

To summarize: the invention relates to a method and apparatus for planning a data acquisition of a region of interest of an object under examination in medical imaging, wherein the region of interest is larger than a region of sensitivity of the medical imaging apparatus. A level of detail corresponding to the user's requirements is enabled in that the planning includes the division of the region of interest into at least two sub-regions based on at least one predefined parameter and raw medical data is recorded from each of the at least two sub-regions.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for generating magnetic resonance (MR) image data, comprising:
   providing an input to a processor that is an electronic designation that specifies a region of interest of an examination subject from which raw MR data are to be acquired by executing an MR data acquisition sequence with an MR scanner that has a region of sensitivity that is smaller than said region of interest, so that said MR scanner is not capable of acquiring said raw MR data from an entirety of said region of interest as a whole;
   also providing said processor with a further electronic input that designates at least one predetermined parameter selected from the group consisting of a parameter used in said data acquisition sequence and a parameter from which a parameter used in said data acquisition sequence is derived;
   in said processor, using said at least one predetermined parameter to automatically divide said region of interest into at least two sub-regions that are each smaller than said region of sensitivity;
   in said processor, automatically defining a final form of said MR data acquisition sequence that causes said raw MR data to be acquired from each of said at least two sub-regions;
   in said processor, generating control signals for said MR scanner corresponding to said final form of said MR data acquisition sequence;
   from said processor, providing said control signals to said MR scanner and thereby changing operation of said MR scanner so as to acquire said raw MR data from each of said at least two sub-regions instead of from said region of interest as a whole; and
   in said processor, reconstructing image data from the raw MR data acquired from said at least two sub-regions, so as to produce an image data set that depicts said region of interest as a whole, and making said image data set available from said computer in electronic form as a data file.

2. A method as claimed in claim 1 wherein said at least one predetermined parameter describes a relationship between said region of interest and said at least two sub-regions.

3. A method as claimed in claim 1 comprising, via a user interface in communication with said processor, receiving a manual entry that defines said at least one predetermined parameter dependent on said examination subject, and using said entry made via said user interface as said further input to said processor.

4. A method as claimed in claim 1 comprising:
   at a display monitor in communication with said processor, displaying a region of interest of the examination subject that is smaller than said region of sensitivity of said medical imaging scanner, and displaying the region of interest that is larger than said region of sensitivity also on said display monitor; and via a user interface in communication with said processor, receiving an input into said processor that adapts the region of interest that is larger than said region of sensitivity.

5. A method as claimed in claim 1 comprising:
via a user interface in communication with said processor, receiving an entry that specifies a property of a sub-region of said at least two sub-regions.

6. A method as claimed in claim 5 comprising:
at a display monitor in communication with said processor, displaying information that spatially relates to said at least two sub-regions.

7. A method as claimed in claim 6 comprising, via said user interface, receiving an input of the specified property of a sub-region that designates a spatial expansion of that sub-region.

8. A method as claimed in claim 7 wherein a first sub-region of said at least two sub-regions differs from an adjacent sub-region of said at least two sub-regions with respect to the property specified by the user for the first sub-region.

9. A method as claimed in claim 8 comprising, in said processor, imposing a restriction with regard to specification of said property of said sub-region via said user interface.

10. A method as claimed in claim 5 comprising, via said user interface, receiving an input that specifies a first property and a second property for at least one sub-region among said at least two sub-regions.

11. A method as claimed in claim 5 comprising, in said processor, enabling premature termination of said specification of said property via said user interface.

12. A method as claimed in claim 11 comprising, following said premature termination, resuming said automatic division of said region of interest into at least two sub-regions, based on said at least one predetermined parameter.

13. A magnetic resonance (MR) apparatus comprising:
an MR scanner having a region of sensitivity;
a processor provided with an input that is an electronic designation that specifies a region of interest of an examination subject from which raw MR data are to be acquired by executing an MR data acquisition sequence with said MR scanner, said region of interest being larger than said region of sensitivity, so that said MR scanner is not capable of acquiring said raw MR data from an entirety of said region of interest as a whole;
said processor also being provided with a further electronic input that designates at least one predetermined parameter selected from the group consisting of a parameter used in said data acquisition sequence and a parameter from which a parameter used in said data acquisition sequence is derived;
said processor being configured to use said at least one predetermined parameter to automatically divide said region of interest into at least two sub-regions that are each smaller than said region of sensitivity;
said processor being configured to automatically define a final form of said MR data acquisition sequence that causes said raw MR data to be acquired from each of said at least two sub-regions;
said processor being configured to generate control signals for said MR scanner corresponding to said final form of said MR data acquisition sequence;
said processor being configured to provide said control signals to said MR scanner and thereby changing operation of said MR scanner so as to acquire said raw MR data from each of said at least two sub-regions instead of from said region of interest as a whole; and
said processor being configured to reconstruct image data from the raw MR data acquired from said at least two sub-regions, so as to produce an image data set that depicts said region of interest as a whole, and to make said image data set available from said processor in electronic form as a data file.

14. A non-transitory, computer-readable data storage medium encoded with programming instructions, said storage medium being loaded into a computer of a magnetic resonance (MR) apparatus comprising an MR scanner that has a region of sensitivity, said programming instructions causing said computer to:
receive an input that is an electronic designation that specifies a region of interest of an examination subject from which raw MR data are to be acquired by executing an MR data acquisition sequence with said MR scanner, said region of interest being larger than said region of sensitivity, so that said MR scanner is not capable of acquiring said raw MR data from an entirety of said region of interest as a whole;
also receive a further electronic input that designates at least one predetermined parameter selected from the group consisting of a parameter used in said data acquisition sequence and a parameter from which a parameter used in said data acquisition sequence is derived;
use said at least one predetermined parameter to automatically divide said region of interest into at least two sub-regions that are each smaller than said region of sensitivity;
automatically define a final form of said MR data acquisition sequence that causes said raw MR data to be acquired from each of said at least two sub-regions;
generate control signals for said MR scanner corresponding to said final form of said MR data acquisition sequence;
provide said control signals to said MR scanner and thereby change operation of said MR scanner so as to acquire said raw MR data from each of said at least two sub-regions instead of from said region of interest as a whole; and
reconstruct image data from the raw MR data acquired from said at least two sub-regions, so as to produce an image data set that depicts said region of interest as a whole, and make said image data set available from said computer in electronic form as a data file.

* * * * *